(12) United States Patent
O'meadhra

(10) Patent No.: US 7,989,667 B2
(45) Date of Patent: Aug. 2, 2011

(54) PROCESSES FOR THE CRYSTALLIZATION OF 2,2,4,4- TETRAMETHYLCYCLOBUTANE-DIOL

(75) Inventor: Ruairi Seosamh O'meadhra, Sierentz (FR)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 12/554,009

(22) Filed: Sep. 4, 2009

(65) Prior Publication Data

US 2010/0063331 A1 Mar. 11, 2010

Related U.S. Application Data

(60) Provisional application No. 61/094,638, filed on Sep. 5, 2008.

(51) Int. Cl.
*C07C 29/145* (2006.01)
(52) U.S. Cl. ...................................................... 568/839
(58) Field of Classification Search ................... 568/839
See application file for complete search history.

(56) References Cited

U.S. PATENT DOCUMENTS 5,169,994 A * 12/1992 Sumner et al. ................ 568/839
5,258,556 A * 11/1993 Sumner et al. ................ 568/839

* cited by examiner

*Primary Examiner* — Brian J Davis
(74) *Attorney, Agent, or Firm* — Louis N. Moreno; Bernard J. Graves, Jr.

(57) ABSTRACT

Disclosed is a novel process for the continuous crystallization of a mixture of cis-2,2,4,4-tetramethylcyclobutanediol and trans-2,2,4,4-tetramethylcyclobutanediol dissolved in a solvent.

41 Claims, 5 Drawing Sheets

US 7,989,667 B2

PROCESSES FOR THE CRYSTALLIZATION OF 2,2,4,4- TETRAMETHYLCYCLOBUTANE-DIOL

CROSS REFERENCE TO RELATED APPLICATIONS

This application claims benefit of the provisional application U.S. Ser. No. 61/094,638, filed Sep. 5, 2008.

DESCRIPTION OF THE INVENTION

1. Field of the Invention

The present disclosure generally relates to a novel process for the continuous crystallization of a mixture of cis-2,2,4,4-tetramethylcyclobutanediol and trans-2,2,4,4-tetramethylcyclobutanediol dissolved in a solvent. In one embodiment, the continuous crystallization processes of the invention yield solid cis-2,2,4,4-tetramethylcyclobutanediol and solid trans-2,2,4,4-tetramethylcyclobutanediol that filters rapidly in high yields and has high product purity.

2. Background of the Invention

U.S. Pat. Nos. 5,258,556 and 5,169,994 describe the isolation of the product from the hydrogenation step (2,2,4,4-tetramethylcyclobutanediol) by either a distillation or crystallization technique. In the examples in these patents, the isolation method by crystallization is described as cooling the filtered, post-hydrogenation mixture to room temperature and separating the product from the solvent.

However, this crystallization method fails to produce a solid product from the post-hydrogenation mixture that can meet a number of stringent criteria necessary for the product to perform satisfactorily in downstream processes. These criteria generally relate to the yield of product, the shape of the crystal size distribution, the east of isolation of the formed crystallization solids, the amount of adhering moisture remaining on the crystal surfaces after filtration, and the moisture content of the filtered product.

In general, the yield of product from a single pass crystallization operation should be maximized. A low yield of dissolved material is both materially and economically inefficient.

Ideally, the shape of the crystal size distribution generated in the crystallization stage should be such that the quantity of "fines" is minimized. "Fines" are particles that tend to plug the pores of the filter or that fill the gaps between larger particles on a filter, which results in reduced flow rate of liquid through the filter. "Fines" particles are known to require long filtration times and to produce dust when dried that provides a safety hazard.

Isolation of the formed crystallization solids is usually performed using a mechanical filtration device, such as a filter or centrifuge. The shape of the crystal size distribution should also be such that the driving force for filtration is minimized and the surface area required for the filtration is also minimized. This would yield a smaller filtration device that can operate at faster filtration rates.

Typically, the amount of adhering moisture remaining on the crystal surfaces after filtration should also be minimized. High surface moisture content increases the probability of impurity entrainment to successive operations.

In general, the moisture content of the filtered product should be low enough so that the successive drying operation has minimum energy demands and requires a short processing time.

U.S. Pat. Nos. 5,258,556 and 5,169,994 describe a batch process to crystallize 2,2,4,4-tetramethylcyclobutanediol from solution. However, for a large scale process, it is more economical to use a continuous process to isolate the product from solution as this eliminates the need for complex heat transfer equipment, seeding protocols and additional storage equipment typically used for batch operations. Continuous processes are also easier to control due to a small dynamic range of operation as compared to batch processing. Accordingly, the present invention is directed to addressing one or more of the needs described above.

SUMMARY OF THE INVENTION

The present disclosure is directed to novel processes for the continuous crystallization of a mixture of cis-2,2,4,4-tetramethylcyclobutanediol and trans-2,2,4,4-tetramethylcyclobutanediol dissolved in a solvent. The continuous crystallization processes of the invention have improved isolated product yield and purity.

In one aspect, the invention relates to a process for the continuous crystallization of a mixture comprising cis-2,2,4,4-tetramethylcyclobutanediol and trans-2,2,4,4-tetramethylcyclobutanediol dissolved in a solvent comprising:

(a) Crystallizing cis-2,2,4,4-tetramethylcyclobutanediol in a first crystallization stage operated at a temperature such that the concentration of trans-2,2,4,4-tetramethylcyclobutanediol in solution is below the saturated concentrations of trans-2,2,4,4-tetramethylcyclobutanediol at the operating temperature of the first stage;

(b) transferring a slurry of crystallized 2,2,4,4-tetramethylcyclobutanediol and the corresponding mother liquor from the first crystallization stage to a second crystallization stage;

(c) crystallizing both cis-2,2,4,4-tetramethylcyclobutanediol and trans-2,2,4,4-tetramethylcyclobutanediol in the second crystallization stage; and (d) separating the crystals from the mother liquor present in the second crystallization stage to yield a mixture of crystallized cis-2,2,4,4-tetramethylcyclobutanediol and crystallized trans-2,2,4,4-tetramethylcyclobutanediol.

In another aspect, the invention relates to a process for the continuous crystallization of a mixture comprising cis-2,2,4,4-tetramethylcyclobutanediol and trans-2,2,4,4-tetramethylcyclobutanediol dissolved in a solvent comprising:

(a) crystallizing cis-2,2,4,4-tetramethylcyclobutanediol in a first crystallization stage operated at a temperature such that the concentration of trans-2,2,4,4-tetramethylcyclobutanediol in solution is below the saturated concentration of trans-2,2,4,4-tetramethylcyclobutanediol at the operating temperature of the first stage;

(b) separating the crystals from the mother liquor present in the first crystallization stage;

(c) removing the crystallized 2,2,4,4-tetramethylcyclobutanediol to yield solid 2,2,4,4-tetramethylcyclobutanediol;

(d) transferring mother liquor obtained from the separation of crystals to a second crystallization stage;

(e) crystallizing both cis-2,2,4,4-tetramethylcyclobutanediol and trans-2,2,4,4-tetramethylcyclobutanediol in the second crystallization stage;and (f) separating the crystals from the mother liquor present in the second crystallization stage to yield a mixture of solid cis-2,2,4,4-tetramethylcyclobutanediol and solid trans-2,2,4,4-tetramethylcyclobutanediol.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
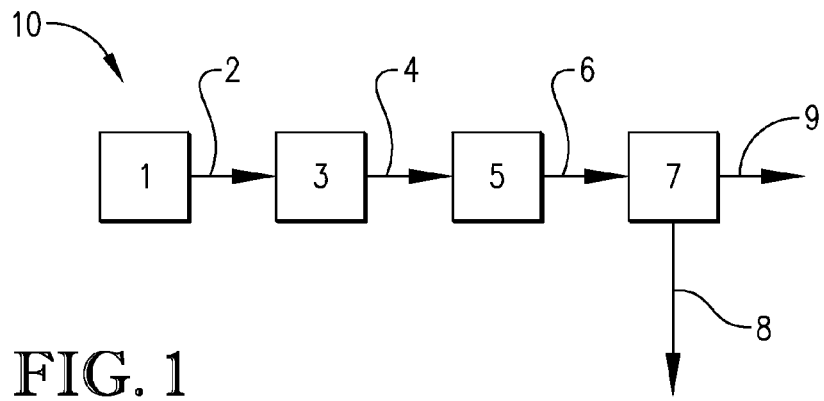
FIG. 1 is a block flow diagram of a continuous two-stage crystallization process with a single product isolation of cis- and trans-2,2,4,4-tetramethylcyclobutane-1,3-diol.

The present disclosure may be understood more readily by reference to the following detailed description of certain embodiments of the invention and the working examples.

In accordance with the purposes of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example, 1,2, 3,4, etc., as well as the endpoints 0 and 10. Also, a range associated with chemical substituent groups such as, for example, "$C_1$ to $C_5$ hydrocarbons," is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the singular forms "a," "an," and "the" include their plural referents unless the context clearly dictates otherwise. For example, reference to the processing or crystallizing of a "mixture," is intended to include the processing or crystallizing making of more than one mixture. References to a composition containing or including "a" given component or product is intended to include other components or products, in addition to the one named.

By "comprising" or "containing" or "including" we mean that at least the named compound, element, particle, or method step, etc., is present in the composition or article or method, but we do not exclude the presence of other compounds, catalysts, materials, particles, method steps, etc., even if the other such compounds, materials, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and it is to be understood that the recited lettering can be arranged in any sequence, unless otherwise indicated.

The invention is directed to novel processes for the continuous crystallization of a mixture of cis-2,2,4,4-tetramethylcyclobutanediol and trans-2,2,4,4-tetramethylcyclobutanediol dissolved in a solvent. The continuous crystallization processes of the invention have improved isolated product yield and purity.

In one aspect of the invention, the method of crystallizing the product is carried out in at least two well-mixed stages of continuous crystallization. The first stage is dedicated to crystallizing the lesser soluble isomer from solution (cis-isomer) while leaving the more soluble isomer (trans-isomer) in solution. The second stage crystallizes most of the remaining cis-isomer from solution and also crystallizes the majority of the trans-isomer from solution.

The operating conditions of each stage in terms of the operating temperature are set such that the fractional crystallization described above the accomplished. Maintaining the process of crystallizing a single isomer in the first stage would normally result in a product with optimal properties. To achieve this, the temperature in the first stage is set such that the concentration of the trans-isomer in solution is below its saturated concentration at the operating temperature of the first stage. "Saturated concentration," as used herein, means the concentration at which no more solid isomer can be dissolved in solution at a given temperature. This will allow an almost pure cis-isomer to crystallize in the first stage while leaving the trans-isomer in solution.

Using typical catalyst systems, the molar ratio of 2,2,4,4-tetramethylcyclobutanediol cis and trans isomers is approximately equal in the resulting solution after the hydrogenation step. Accordingly, in one embodiment of the invention, the molar ratio of cis and trans isomers in the solution to be crystallized is approximately equal.

In one embodiment of the invention, the residence time is at least 0.5 hours in each stage of crystallization. Under the experimental conditions described in the Examples below, a residence time of at least 0.5 hours provided optimal yields of crystallized product. If the residence time was much less than 0.5 hours, there was not enough time for the material in solution to crystallize due to mass transfer limitations. In one embodiment, the residence time in each crystallization stage is independently at least 0.5 hours. In another embodiment, the residence time in each crystallization stage is independently from 0.5 to four hours. In another embodiment, the residence time in each crystallization stage is independently from one to three hours.

In one embodiment, the process relates to a continuous two-stage crystallization operation with a single product isolation of cis- and trans-2,2,4,4-tetramethylcyclobutanediol as shown in FIG. 1. The hydrogenation-crystallization system 10 has a hydrogenation reactor 1 which feeds crude 2,2,4,4-tetramethylcyclobutane-1,3-diol via the first stage crystallization feed line 2 to the first stage crystallizer 3. The first stage crystallizer 3 feeds a slurry via the second stage crystallization feed line 4 to the second stage crystallizer 5. The second stage crystallizer 5 feeds the solid liquid separator 7 via the solid liquid separation feed line 6. Solids are removed from the solid liquid separator 7 via the solids removal line 8. Mother liquor and wash filtrate are removed from the solid liquid separator 7 via line 9. In the first crystallization stage, the temperature is below the saturation temperature of the cis-2,2,4,4-tetramethylcyclobutanediol. A slurry of the cis-2,2,4,4-tetramethylcyclobutanediol and the solution containing dissolved trans-2,2,4,4-tetramethylcyclobutanediol and the remaining dissolved cis-2,2,4,4-tetramethylcyclobutane-1,3-diol is transferred from the first crystallization stage to the second crystallization stage. In the second crystallization stage, the temperature is below the saturation temperature of both the cis- and the trans-2,2,4,4-tetramethylcyclobutanediols resulting in the formation of a slurry containing both the cis- and the trans-2,2,4,4-tetramethylcyclobutanediols. The slurry containing both the cis- and the trans-2,2,4,4-tetramethylcyclobutanediols in the solvent is transferred to a solid-liquid separation unit. In this embodiment, only the slurry from the second stage of operation is subjected to a solid-liquid separation operation whereby essentially pure solids with a mixture of cis- and trans-2,2,4,4-tetramethylcyclobutanediol are isolated having a combined purity of at least 99.0% by weight. In another embodiment, the combined purity of the mixture of cis- and trans-2,2,4,4-tetramethylcyclobutanediol isolated and dried is at least 99.80% by weight.

Figure 2:
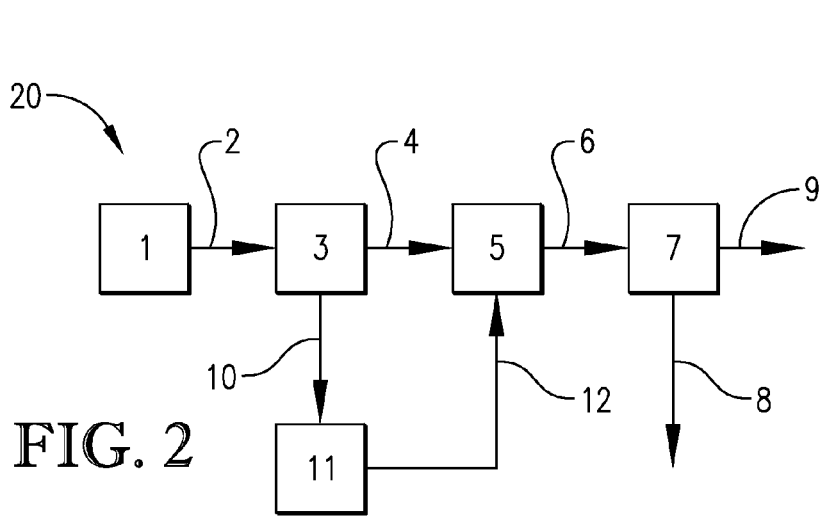
FIG. 2 is a block flow diagram of a continuous two-stage crystallization process with a single product isolation of a cis- and trans-2,2,4,4-tetramethylcyclobutane-1,3-diol and having a mother liquor advance system included in the first crystallization stage.

In another embodiment, the process relates to a continuous two-stage crystallization operation with a single product isolation of cis- and trans-2,2,4,4-tetramethylcyclobutanediol, as shown in FIG. 2. The hydrogenation-crystallization system 20 has a hydrogenation reactor 1 which feeds crude 2,2,4,4-tetramethylcyclobutane-1,3-diol via the first stage crystallization feed line 2 to the first stage crystallizer 3. The first stage crystallizer 3 feeds a slurry via the second stage crystallization feed line 4 to the second stage crystallizer 5. The second stage crystallizer 5 feeds the solid liquid separator 7 via the solid liquid separation feed line 6. Solids are removed from the solid liquid separator 7 via the solids removal line 8. Mother liquor is removed from the first stage crystallizer 3 via mother liquor feed line 10 to a mother liquor separation zone 11. The mother liquor is transferred to the second stage crystallizer 5 via a mother liquor advance line 12. In the first crystallization stage, the temperature is below the saturation temperature of the cis-2,2,4,4-tetramethylcyclobutanediol. A slurry of the cis-2,2,4,4-tetramethylcyclobutanediol and the solution containing dissolved trans-2,2,4,4-tetramethylcyclobutanediol and remaining dissolved cis-2,2,4,4-tetramethylcyclobutane-1,3-diol is transferred from the first crystallization stage to the second crystallization stage. In the second crystallization stage, the temperature is below the saturation temperature of both the cis- and the trans-2,2,4,4-tetramethylcyclobutanediols resulting in the formation of a slurry containing both the cis- and the trans-2,2,4,4-tetramethylcyclobutanediols. The slurry containing both the cis- and the trans-2,2,4,4-tetramethylcyclobutanediols in the solvent is transferred to a solid-liquid separation unit. In the first crystallization stage, a mother liquor advance system is used, in which the temperature is below the saturation temperature of the cis-2,2,4,4-tetramethylcyclobutane-1,3-diol. Two product streams are removed from the first stage of crystallization and, ultimately, are both fed to the second stage. One stream is removed from the first stage crystallizer and comprises the slurry of 2,2,4,4-tetramethylcyclobutane-1,3-diol. The second stream is removed from a separate zone within the first stage crystallizer where a crystal-free mother liquor stream is generated. The advantage of this embodiment is that the residence time of the solids produced in the first stage crystallizer can be regulated separately from the residence time of the mother liquor. This net result allows the solids content of the first stage crystallizer to be controlled independent of all other operating variables relating to that stage of crystallization. This has an advantage in forming larger crystals due to the increased residence time. It also allows for smoother operation as the probability of heat exchanger fouling is reduced. In addition, this embodiment may permit the optional removal of a slurry product from the first stage of crystallization in order to isolate a pure cis-isomer product.

Figure 3:
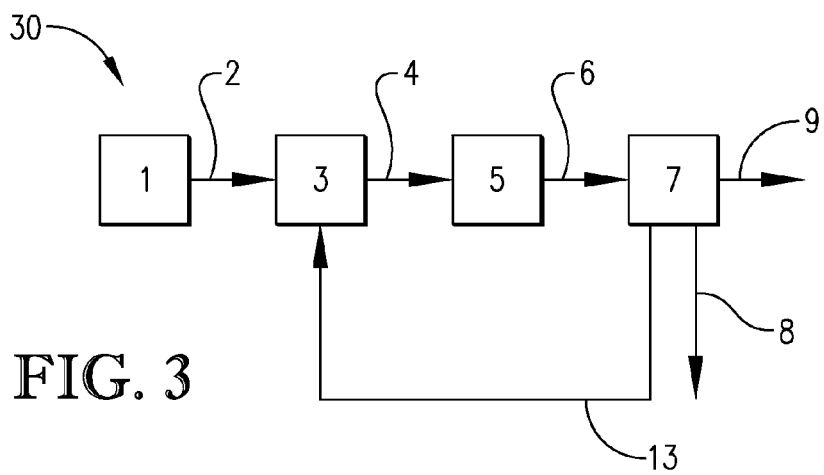
FIG. 3 is a block flow diagram of a continuous crystallization process with a single product isolation of cis- and trans-2,2,4,4-tetramethylcyclobutane-1,3-diol and solids recycle to increase solids content in the first stage of crystallization.

In another embodiment, the process relates to a continuous two-stage crystallization operation with a single product isolation of cis- and trans-2,2,4,4-tetramethylcyclobutanediol. This embodiment provides for a partial recycle of solids from the second stage of crystallization (post solid-liquid separation) to the first stage of crystallization, as shown in FIG. 3. The hydrogenation-crystallization system 30 has a hydrogenation reactor 1 which feeds crude 2,2,4,4-tetramethylcyclobutane-1,3-diol via the first stage crystallization feed line 2 to the first stage crystallizer 3. The first stage crystallizer 3 feeds a slurry vial the second stage crystallization feed line 4 to the second stage crystallizer 5. The second stage crystallizer 5 feeds the solid liquid separator 7 via the solid liquid separation feed line 6. Solids are removed from the solid liquid separator 7 via the solids removal line 8. The solids recycle line 13 transfers solids from the solid liquid separator 7 back to the first stage crystallizer 3. In the first crystallization stage, the temperature is below the saturation temperature of the cis-2,2,4,4-tetramethylcyclobutanediol. The recycled solids will include both cis- and trans-isomer. This embodiment has two advantages. First, similar in result to the embodiment shown in FIG. 2, the solids content in the first stage crystallizer is increased, promoting the formation of larger particles. Second, the fact that the trans-isomer, along with the cis-isomer, is being recycled to the first stage means that both cis- and trans-isomer are present as solids in the first stage. This will allow the temperature of the first stage crystallizer to be varied below the saturation temperature of the trans-isomer as trans-isomer will not nucleate as separate crystals but will grow on the already existing surface area of trans-isomer present.

Figure 4:
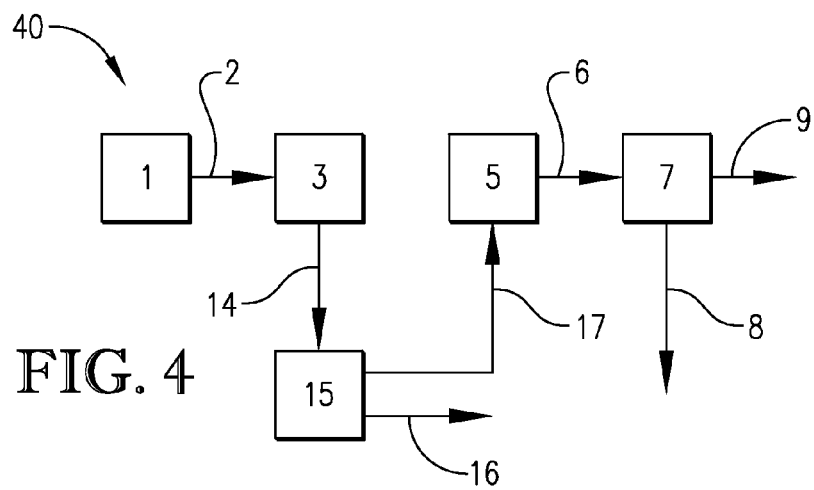
FIG. 4 is a block flow diagram of a continuous two-stage crystallization process with separate isolation of a cis-2,2,4,4-tetramethylcyclobutane-1,3-diol and another isolation of a mixture of cis- and trans-tetramethylcyclobutane-1,3-diol.

In another embodiment, the process relates to a continuous two-stage crystallization operation with separate isolation of a cis-2,2,4,4-tetramethylcyclobutanediol product and another isolation of a cis- and trans-2,2,4,4-tetramethylcyclobutanediol product as shown FIG. 4. In this embodiment, advantage can be taken of the fact that only cis-2,2,4,4-tetramethylcyclobutanediol crystallizes in the first stage of crystallization to remove a separate stream from the crystallizer to isolate a pure cis-isomer fraction. After the crystallized cis-2,2,4,4-tetramethylcyclobutanediol is removed, the mother liquor from the isolation step can then be forwarded to the second stage of crystallization to crystallize a mixture of cis- and trans-2,2,4,4-tetramethylcyclobutanediol.

Figure 9:
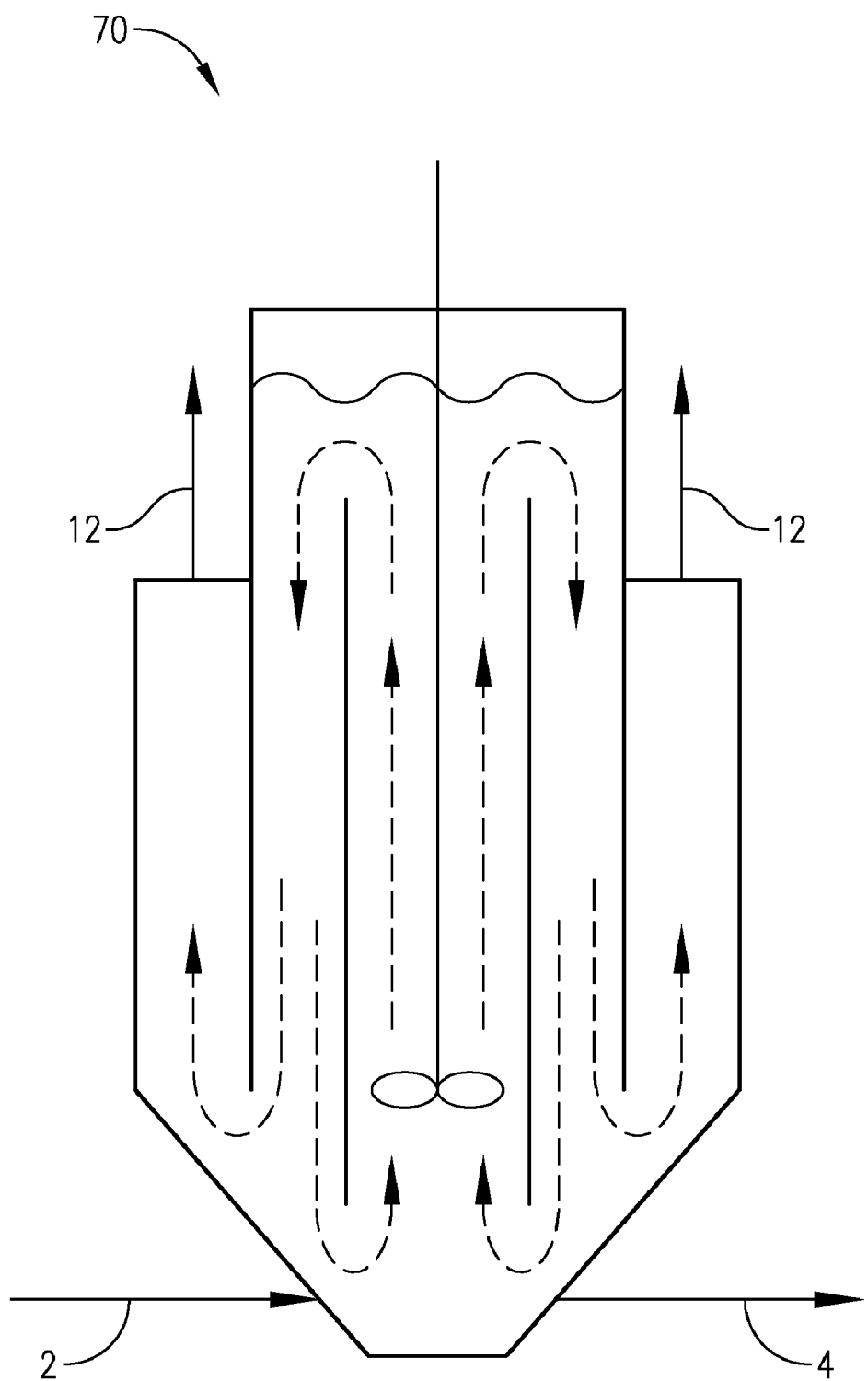
FIG. 9 is an example of a zoned crystallization system where two product streams are removed from crystallization system.

FIG. 9 shows a zoned crystallization system where two product streams are removed from a crystallization system, as shown in FIG. 4. The hydrogenation-crystallization system 40 has a hydrogenation reactor 1 which feeds crude 2,2,4,4-tetramethylcyclobutane-1,3-diol via the first stage crystallization feed line 2 to the first stage crystallizer 3. The first stage crystallizer 3 feeds a slurry via the second solid liquid separation feed line 14 to the first solid liquid separator 15. Solids are removed from the first solid liquid separator 15 via solids separation line 16 and mother liquor from the first solid liquid separator 15 via line 17 are sent to the second stage crystallizer 5. The second stage crystallizer 5 feeds the solid liquid separator 7 via the solid liquid separation feed line 6. Solids are removed from the second solid liquid separator 7 via the solids removal line 8. Mother liquor and wash filtrate are removed from the second solid liquid separator 7 via line 9. In the first crystallization stage, the temperature is below the saturation temperature of the cis-2,2,4,4-tetramethylcyclobutanediol. A crystal free stream is removed from the quiescent region of a crystallizer, above the point where solids have been allowed to settle by gravity from a pure mother liquor stream. A crystal rich stream is then removed from the bottom of the crystallizer.

Figure 5:
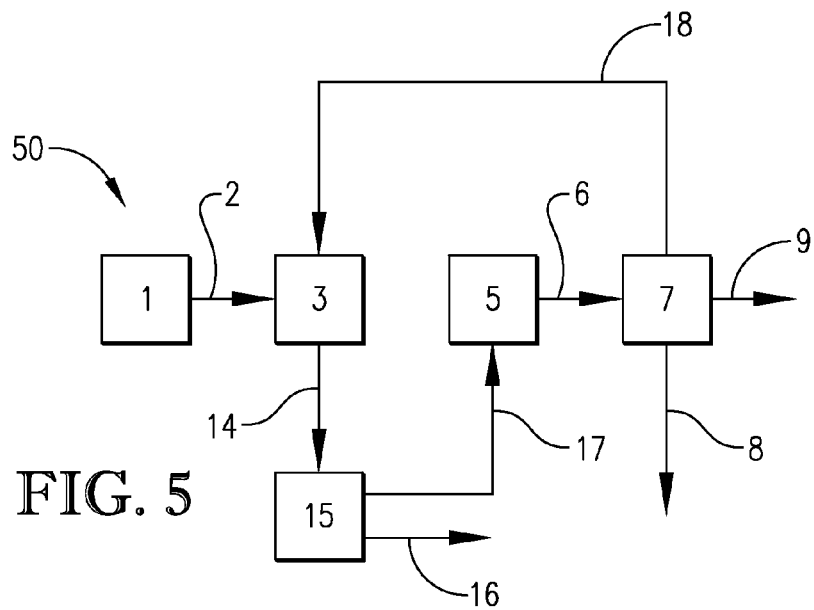
FIG. 5 is a block flow diagram of a continuous two-stage crystallization process with two product isolation points of cis- and trans-2,2,4,4-tetramethylcyclobutane-1,3-diol and including a recycle to increase solids content in the first stage of crystallization.

In another embodiment, the process relates to a continuous two-stage crystallization operation with two product isolation points of cis- and trans-2,2,4,4-tetramethylcyclobutanediol, as shown in FIG. 5. The hydrogenation-crystallization system 50 has a hydrogenation reactor 1 which feeds crude 2,2,4,4-tetramethylcyclobutane-1,3-diol via the first stage crystallization feed line 2 to the first stage crystallizer 3. The first stage crystallizer 3 feeds a slurry via the first solid liquid separation feed line 14 to the first solid liquid separator 15. Solids are removed from the first solid liquid separator 15 via solids separation line 16 and mother liquor from the first solid liquid separator 15 via line 17 and sent to the second stage crystallizer 5. The second stage crystallizer 5 feeds the solid second liquid separator 7 via the second solid liquid separation feed line 6. Solids are removed from the second solid liquid separator 7 via the solids removal line 8 or recycled to the first stage crystallizer 3 via solids recycle line 18. Mother liquor and wash filtrate are removed from the second solid liquid separator 7 via line 9. The first product removal point is from the first stage of crystallization from which cis-2,2,4,4-tetramethylcyclobutane-1,3-diol is removed, and the second is from the second stage of crystallization from which a mixture of cis- and trans-2,2,4,4-tetramethylcyclobutane-1,3-diol is removed. Isolating solids at higher temperatures has advantages in terms of filtration rate and product purity. At higher temperatures, i.e., the higher temperature of the first stage crystallizer relative to the lower temperature of the second stage crystallizer, the mother liquor viscosity is typically lower, which allows for faster filtration times. In addition, a more pure product can be expected since impurities are typically more soluble at higher temperatures thus resulting in a more pure product. The mother liquor from the solid-liquid isolation step is fed to the second stage crystallizer in this embodiment to maximize product yield. As in the embodiment shown in FIG. 3, this embodiment also provides for a partial recycle of solids from the second stage of crystallization (post solid-liquid separation) to the first stage of crystallization.

Figure 6:
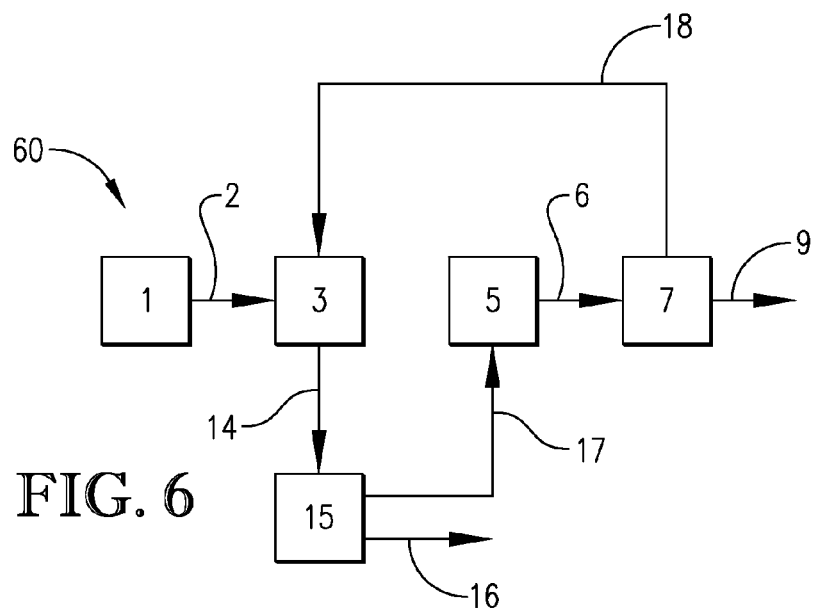
FIG. 6 is a block flow diagram of a continuous two-stage crystallization process with one product isolation point of cis- and trans-2,2,4,4-tetramethylcyclobutane-1,3-diol and includes solids recycle to increase solids content in the first stage of crystallizations.

In another embodiment, the process relates to a continuous two-stage crystallization operation with two product isolation points of cis- and trans-2,2,4,4-tetramethylcyclobutanediol, as shown in FIG. 6. The hydrogenation-crystallization system 60 has a hydrogenation reactor 1 which feeds crude 2,2,4,4-tetramethylcyclobutane-1,3-diol via the first stage crystallization feed line 2 to the first stage crystallizer 3. The first stage crystallizer 3 feeds a slurry via the first solid liquid separation feed line 14 to the first solid liquid separator 15. Solids are removed from the first solid liquid separator 15 via solids separation line 16 and mother liquor from the first solid liquid separator 15 via line 17 and sent to the second stage crystallizer 5. The second stage crystallizer 5 feeds the second solid liquid separator 7 via the second solid liquid separation feed line 6. Solids are recycled via solids recycle line 18 to the first stage crystallizer line 8. Mother liquor and wash filtrate are removed from the second solid liquid separator 7 via line 9. In this embodiment, the entire product is isolated from the first stage of crystallization and all of the solids from the second stage isolation step are recycled to the first stage crystallization. This solids recycle step is included to increase solids content and/or the size of the crystals of cis- and trans-2,2,4,4-tetramethylcyclobutanediol in first stage of crystallization. This embodiment results in mostly pure product since isolating product at a higher temperature, i.e., the higher temperature of the first stage crystallizer relative to the lower temperature of the second stage crystallizer, results in a more pure product.

For the purposes of this disclosure, the term "wt" means "weight."

The invention is further described by the following embodiments.

A process for the continuous crystallization of a mixture comprising cis-2,2,4,4-tetramethylcyclobutanediol and trans-2,2,4,4-tetramethylcyclobutanediol dissolved in a solvent comprising:

(a) crystallizing cis-2,2,4,4-tetramethylcyclobutanediol in a first crystallization stage operated at a temperature such that the concentration of trans-2,2,4,4-tetramethylcyclobutanediol in solution is below the saturated concentration of trans-2,2,4,4-tetramethylcyclobutanediol at the operating temperature of the first stage;

(b) transferring a slurry of crystallized cis-2,2,4,4-tetramethylcyclobutanediol and the corresponding mother liquor from the first crystallization stage to a second crystallization stage;

(c) crystallizing both cis-2,2,4,4-tetramethylcyclobutanediol and trans-2,2,4,4-tetramethylcyclobutanediol in the second crystallization stage; and (d) separating the crystals the cis-2,2,4,4-tetramethylcyclobutanediol and trans-2,2,4,4-tetramethylcyclobutanediol from the mother liquor present in the second crystallization stage to yield a mixture of crystallized cis-2,2,4,4-tetramethylcyclobutanediol and crystallized trans-2,2,4,4-tetramethylcyclobutanediol.

The process according to the previous embodiment in paragraph 60, wherein the solvent is isobutyl isobutyrate.

The process according to any of the preceding embodiments in paragraphs 60-64, wherein the mixture comprising cis-2,2,4,4-tetramethylcyclobutanediol and trans-2,2,4,4-tetramethylcyclobutanediol dissolved in a solvent is the result of the hydrogenation of 2,2,4,4-tetramethylcyclobutanedione The process according to any of the preceding embodiments in paragraphs 60 and 64-65, wherein the concentration of cis-2,2,4,4-tetramethylcyclobutanediol in the mixture to be subjected to crystallization is from 5 to 15 wt % or 5 to 25 wt % with respect to the total weight of the mixture and the concentration of trans-2,2,4,4-tetramethylcyclobutanediol in the mixture to be subjected to crystallization is from 5 to 15 wt % or 5 to 25 wt % with respect to the total weight of the mixture.

The process according to any of the preceding embodiments in paragraphs 60 and 64-66, wherein the residence time in each crystallization stage is independently at least 0.5 hours.

The process according to any of the preceding embodiments in paragraphs 60 and 64-67, wherein the residence time in each crystallization stage is independently from 0.5 to four hours.

The process according to any of the preceding embodiments in paragraphs 60 and 64-68, further comprising removing crystallized cis-2,2,4,4-tetramethylcyclobutanediol from the first crystallization stage to yield solid cis-2,2,4,4-tetramethylcyclobutanediol.

The process according to any of the preceding embodiments in paragraphs 60 and 64-69, wherein the rate of transfer of the slurry of crystallized 2,2,4,4-tetramethylcyclobutanediol from the first crystallization stage to the second crystallization stage is slower than the rate of the transfer of the mother liquor from the first crystallization stage to the second crystallization stage.

The process according to any of the preceding embodiments in paragraphs 60 and 64-70, wherein the combined purity of the isolated, dried mixture of crystallized cis- and trans-2,2,4,4-tetramethylcyclobutanediol is at least 99.0%.

The process according to any of the preceding embodiments in paragraphs 60 and 64-71, wherein the combined purity of the isolated, dried mixture of crystallized cis- and trans-2,2,4,4-tetramethylcyclobutanediol is at least 99.8%.

The process according to any of the preceding embodiments in paragraphs 60 and 64-72, further comprising:
(a) recycling a fraction of the mixture of crystallized cis and trans 2,2,4,4-tetramethylcyclobutanediol from the second crystallization stage to the first crystallization stage; and
(b) growing crystals of trans-2,2,4,4-tetramethylcyclobutanediol in the first crystallization stage.

The process according to any of the preceding embodiments in paragraphs 60 and 64-73, wherein the solvent is isobutyl isobutyrate.

The process according to any of the preceding embodiments in paragraphs 60, 64-73 and 76, wherein the mixture comprising cis-2,2,4,4-tetramethylcyclobutanediol and trans-2,2,4,4-tetramethylcyclobutanediol dissolved in a solvent is the result of the hydrogenation of 2,2,4,4-tetramethylcyclobutanedione.

The process according to any of the preceding embodiments in paragraphs 60, 64-73, and 76-77, wherein the concentration of cis-2,2,4,4-tetramethylcyclobutanediol in the mixture from 5 to 15 wt % or 5 to 25 wt % with respect to the total weight of the mixture and the concentration of trans-2,2,4,4-tetramethylcyclobutanediol in the mixture is from 5 to 15 wt % or 5 to 25 wt % with respect to the total weight of the mixture.

The process according to any of the preceding embodiments in paragraphs 60, 64-73, and 76-78, wherein the residence time in each crystallization stage is independently at least 0.5 hours.

The process according any of the preceding embodiments in paragraphs 60, 64-73, and 76-79, wherein the residence time in each crystallization stage is independently from 0.5 to four hours.

The process according to any of the preceding embodiments in paragraphs 60, 64-73, and 76-80, wherein the residence time in each crystallization stage is independently from one to three hours.

The process according to any of the preceding embodiments in paragraphs 60, 64-73, and 76-81, wherein the first crystallization stage is operated at a temperature below the saturation temperature of trans-2,2,4,4-tetramethylcyclobutanediol.

A process for the continuous crystallization of a mixture comprising cis-2,2,4,4-tetramethylcyclobutanediol and trans-2,2,4,4-tetramethylcyclobutanediol dissolved in a solvent, the process comprising:
(a) crystallizing cis-2,2,4,4-tetramethylcyclobutanediol in a first crystallization stage operated at a temperature such that the concentration of trans-2,2,4,4-tetramethylcyclobutanediol in solution is below the saturated concentration of trans-2,2,4,4-tetramethylcyclobutanediol at the operating temperature of the first stage;
(b) separating the crystals of cis-2,2,4,4-tetramethylcyclobutanediol from the mother liquor present in the first crystallization stage;
(c) removing the crystallized cis-2,2,4,4-tetramethylcyclobutanediol to yield solid cis-2,2,4,4-tetramethylcyclobutanediol;
(d) transferring mother liquor obtained from the separation of crystals of cis-2,2,4,4-tetramethylcyclobutanediol to a second crystallization stage;
(e) crystallizing both cis-2,2,4,4-tetramethylcyclobutanediol and trans-2,2,4,4-tetramethylcyclobutanediol in the second crystallization stage; and
(f) separating the crystals of cis-2,2,4,4-tetramethylcyclobutanediol and trans-2,2,4,4-tetramethylcyclobutanediol from the mother liquor present in the second crystallization stage to yield a mixture of solid cis-2,2,4,4-tetramethylcyclobutanediol and solid trans-2,2,4,4-tetramethylcyclobutanediol.

The process according to the previous embodiment in paragraph 83, wherein the solvent is isobutyl isobutyrate.

The process according to any of the preceding embodiments in paragraphs 83 and 90, wherein the mixture comprising cis-2,2,4,4-tetramethylcyclobutanediol and trans-2,2,4,4-tetramethylcyclobutanediol dissolved in a solvent is the result of the hydrogenation of 2,2,4,4-tetramethylcyclobutanedione.

The process according to any of the preceding embodiments in paragraphs 83 and 90-91, wherein the concentration of cis-2,2,4,4-tetramethylcyclobutanediol in the mixture is from 5 to 15 wt % or 5 to 25 wt % with respect to the total weight of the mixture and the concentration of trans-2,2,4,4-tetramethylcyclobutanediol in the mixture is from 5 to 15 wt % or 5 to 25 wt % with respect to the total weight of the mixture.

The process according to any of the preceding embodiments in paragraphs 83 and 90-92, wherein the residence time in each crystallization stage is independently at least 0.5 hours.

The process according to any of the preceding embodiments in paragraphs 83 and 90-93, wherein the residence time in each crystallization stage is independently from 0.5 to four hours.

The process according to any of the preceding embodiments in paragraphs 83 and 90-94, wherein the residence time in each crystallization stage is independently from one to three hours.

The process according to any of the preceding embodiments in paragraphs 83 and 90-95, wherein the combined purity of the isolated, dried mixture of crystallized cis- and trans-2,2,4,4-tetramethylcyclobutanediol is at least 99.0%.

The process according to any of the preceding embodiments in paragraphs 83 and 90-96, wherein the combined purity of the isolated, dried, mixture of crystallized cis- and trans-2,2,4,4-tetramethylcyclobutanediol is at least 99.8%.

The process according to any of the preceding embodiments in paragraphs 83 and 90-97, further comprising:
(a) recycling a fraction of the mixture of crystallized cis and trans 2,2,4,4-tetramethylcyclobutanediol from the second crystallization stage to the first crystallization stage; and
(b) growing crystals of trans-2,2,4,4-tetramethylcyclobutanediol in the first crystallization stage.

The process according to any of the preceding embodiments in paragraphs 83 and 90-98, wherein the solvent is isobutyl isobutyrate.

The process according to any of the preceding embodiments in paragraphs 83, 90-98 and 101, wherein the mixture comprising cis-2,2,4,4-tetramethylcyclobutanediol and trans-2,2,4,4-tetramethylcyclobutanediol dissolved in a solvent is the result of the hydrogenation of 2,2,4,4-tetramethylcyclobutanedione.

The process according to any of the preceding embodiments in paragraphs 83, 90-98 and 101-102, wherein the concentration of cis-2,2,4,4-tetramethylcyclobutanediol in the mixture is from 5 to 15 wt % or 5 to 25 wt % with respect to the total weight of the mixture and the concentration of trans-2,2,4,4-tetramethylcyclobutanediol in the mixture is from 5 to 15 wt % or 5 to 25 wt % with respect to the total weight of the mixture.

The process according to any of the preceding embodiments in paragraphs 83, 90-98 and 101-103, wherein the residence time in each crystallization stage is independently at least 0.5 hours.

The process according to any of the preceding embodiments in paragraphs 83, 90-98 and 101-104, wherein the residence time in each crystallization stage is independently from 0.5 to four hours.

The process according to any of the preceding embodiments in paragraphs 83, 90-98 and 101-105, wherein the residence time in each crystallization stage is independently from one to three hours.

The process according to any of the preceding embodiments in paragraphs 83, 90-98 and 101-106, wherein the first crystallization stage is operated at a temperature below the saturation temperature of trans-2,2,4,4-tetramethylcyclobutanediol.

The process according to any of the preceding embodiments in paragraphs 83, 90-98 and 101-107, wherein the combined purity of the isolated, dried mixture of crystallized cis- and trans-2,2,4,4-tetramethylcyclobutanediol is at least 99.0%.

The process according to any of the preceding embodiments in paragraphs 83, 90-98 and 101-108, wherein the combined purity of the isolated, dried mixture of crystallized cis- and trans-2,2,4,4-tetramethylcyclobutanediol is at least 99.8%.

The process according to any of the preceding embodiments in paragraphs 83, 90-98 and 101-109, wherein the crystallized 2,2,4,4-tetramethylcyclobutanediol from the second crystallization stage is completely recycled to the first crystallization stage.

The process according to any of the preceding embodiments in paragraphs 83, 90-98 and 101-110, wherein the solvent is isobutyl isobutyrate.

The process according to any of the preceding embodiments in paragraphs 83, 90-98 and 101-111, wherein the mixture comprising cis-2,2,4,4-tetramethylcyclobutanediol and trans-2,2,4,4-tetramethylcyclobutanediol dissolved in a solvent is the result of the hydrogenation of 2,2,4,4-tetramethylcyclobutanedione.

The process according to any of the preceding embodiments in paragraphs 83, 90-98 and 101-112, wherein the concentration of cis-2,2,4,4-tetramethylcyclobutanediol in the mixture from 5 to 15 wt % or 5 to 25 wt % with respect to the total weight of the mixture and the concentration of trans-2,2,4,4-tetramethylcyclobutanediol is from 5 to 15 wt % or 5 to 25 wt % with respect to the total weight of the mixture.

The process according to any of the preceding embodiments in paragraphs 83, 90-98 and 101-113, wherein the residence time in each crystallization stage is independently at least 0.5 hours.

The process according to any of the preceding embodiments in paragraphs 83, 90-98 and 101-114, wherein the residence time in each crystallization stage is independently from 0.5 to four hours.

The process according to any of the preceding embodiments in paragraphs 83, 90-98 and 101-115, wherein the residence time in each crystallization stage is independently from one to three hours.

The process according to any of the preceding embodiments in paragraphs 83, 90-98 and 101-116, wherein the first crystallization stage is operated at a temperature below the saturation temperature of trans-2,2,4,4-tetramethylcyclobutanediol.

The process according to any of the preceding embodiments in paragraphs 83, 90-98 and 101-117, wherein the combined purity of the isolated, dried mixture of crystallized cis- and trans-2,2,4,4-tetramethylcyclobutanediol is at least 99.0%.

The process according to any of the preceding embodiments in paragraphs 83, 90-98 and 101-118, wherein the combined purity of the isolated, dried mixture of crystallized cis- and trans-2,2,4,4-tetramethylcyclobutanediol is at least 99.8%.

The following examples further illustrate how the continuous crystallization processes of the invention can be conducted and evaluated, and are intended to be purely exemplary of the invention and are not intended to limit the scope thereof. Unless indicated otherwise, parts are parts by weight, temperature is in degrees C. or is at room temperature, and pressure is at or near atmospheric pressure.

EXAMPLES

The term "semi-continuous," as used herein, describes a process where there is an intermittent feed to the crystallizer and an intermittent product stream discharge. From the information described in the specification and these Examples, one of skill in the art would be able to design a continuous batch or a continuous crystallization process. Data for the solubility curve and the meta-stable zone width are fundamental to the design and operation of any crystallization system. They allow one to specify: (i) the optimum number of stages in a continuous process to maximize the particle size and filtration properties of the slurry; (ii) steady-state operating temperatures of continuous crystallization stages to yield maximum energy efficiency and product yield; (iii) optimally size heat exchanger units based on maximum allowable temperature differences that avoid issues with heat exchanger surface scaling; (iv) mixing requirements for the individual crystallizer unit operations; and (v) minimum residence time requirements to achieve an optimal yield of products.

The abbreviation "TMCD," as used herein, represents 2,2,4,4-tetramethylcyclobutanediol. The abbreviation "ML," as used herein, represents mother liquor.

All of the solubility data and concentrations of cis and trans TMCD were measured by gas chromotography (GC) using an Agilent 6890GC instrument. The instrument was equipped with a split-splitless injector and flame ionization detection. The column is a DB®-Wax, 30 meter×0.25 mm ID, 0.50 μm film thickness column. The cis/trans ratio of the compositions was calculated from the respective concentrations.

The charge concentration of the isomers is expressed as weight % relative to the saturated concentration of each isomer at a temperature of 62.6° C.

Examples 1 and 2 describe the procedure and results for measuring the solubility and meta-stable zone widths of cis- and trans-2,2,4,4-tetramethylcyclobutanediol in isobutyl isobutyrate solvent.

Example 1

The solubility of cis- and trans-2,2,4,4-tetramethylcyclobutanediol in isobutyl isobutyrate was determined by charging 800 grams of a solution containing 100 relative weight % cis-2,2,4,4-tetramethylcyclobutanediol and 69 relative weight % trans-2,2,4,4-tetramethylcyclobutanediol in isobutyl isobutyrate solvent to a 1.2 L jacketed glass vessel. The charge concentration of the isomers is expressed as weight % relative to the saturated concentration of each isomer at a temperature of 62.6° C. The vessel was equipped with a 4-blade flat blade pitched impeller for solids suspension, and the jacket was used to control the temperature of the vessel contents. The vessel was equipped with charging and sampling ports on top and a valve at the base to drain the vessel contents.

The slurry was allowed to stand for one hour sufficient for the solids to saturate the solvent at 6.4° C. At that time, a sample of the solution was drawn from the cell using a fritted pipette so as to remove only the liquid phase. The sample was analyzed for cis and trans isomer content. These values represented the saturated concentration of each isomer at the sampling temperature.

The cell contents were heated to 10.2° C. and the contents were held for a further hour to allow the slurry to equilibrate. A sample was then taken of the solution and analyzed. Following this procedure, data was gathered to 62.6° C. The results for each temperature point are reported in Table 1.

TABLE 1

Relative Solubility of cis- and trans-2,2,4,4-tetramethylcyclobutanediol in isobutyl isobutyrate

| Sample | Temperature [° C.] | Cis Solubility [Relative wt %] | Trans Solubility [Relative wt %] |
|---|---|---|---|
| 1 | 6.4 | 0 | 1 |
| 2 | 10.2 | 3 | 3 |
| 3 | 19 | 10 | 10 |
| 4 | 26.2 | 17 | 19 |
| 5 | 34.7 | 29 | 32 |
| 6 | 39.6 | 37 | 41 |
| 7 | 44.5 | 47 | 52 |
| 8 | 51.6 | 64 | 69 |
| 9 | 58.8 | 86 | 89 |
| 10 | 62.6 | 100 | 100 |

Figure 7:
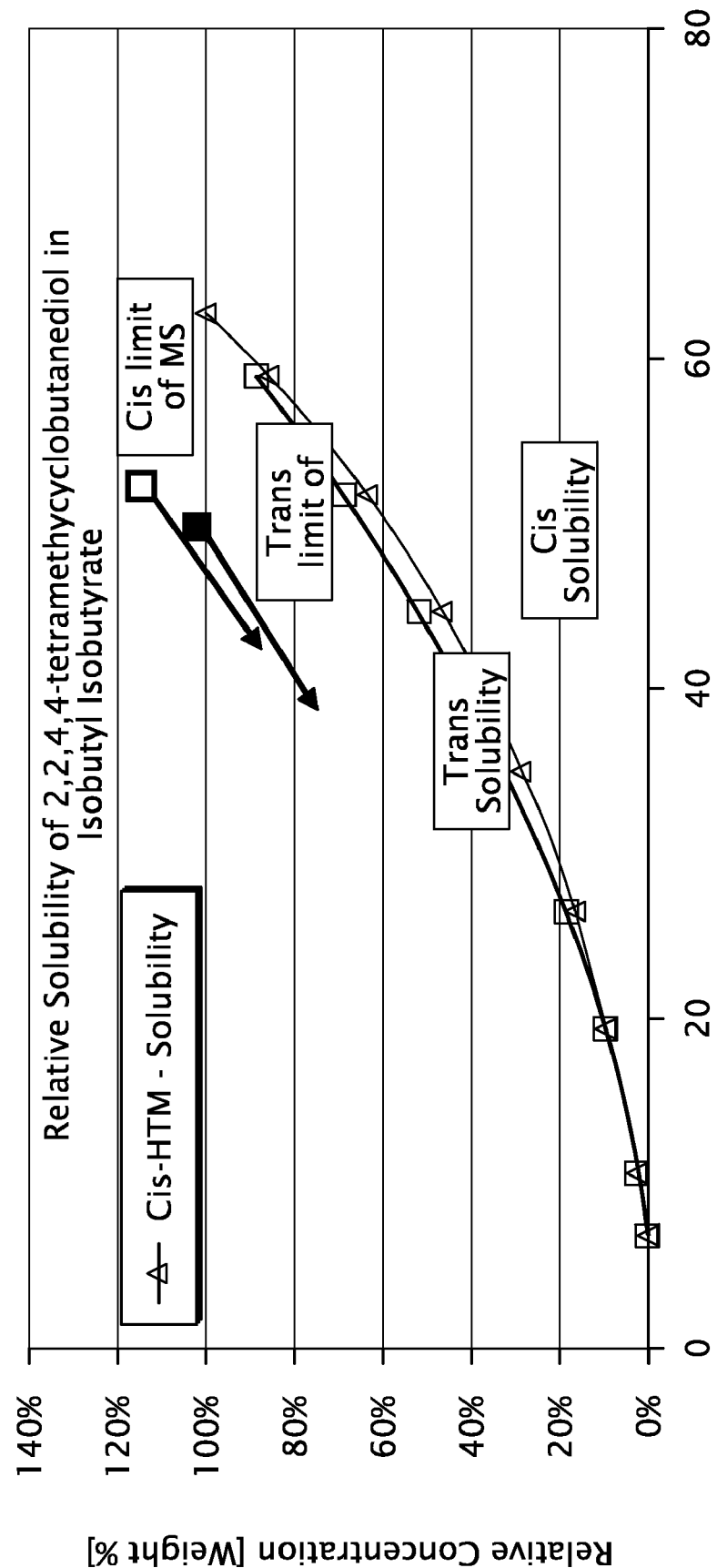
FIG. 7 is a graph showing the relative solubility of cis- and trans2,2,4,4-tetramethylcyclobutanediol in isobutyl isobutyrate.

The data from Table 1 is plotted in FIG. 7. FIG. 7 is a graph showing the relative solubility of cis- and trans-2,2,4,4-tetramethylcyclobutanediol in isobutyl isobutyrate and the trans and cis limits of the meta-stable zone. Also shown in FIG. 7 is the limit of the meta-stable region. Derivation of the meta-stable limit is described in Example 2.

Table 1A shows the saturated temperature of each isomer extrapolated from the data shown in FIG. 7. Table 1A also lists the limit of the meta-stable zone width for each isomer.

TABLE 1A

Meta-stable zone limit data points shown in FIG. 7

| Compound | Saturated Temperature [° C.] | Limit of Meta-Stable Zone Width [° C.] |
|---|---|---|
| Cis-2,2,4,4-tetramethylcyclobutanediol | 68 | 58.24 |
| Trans-2,2,4,4-tetramethylcyclobutanediol | 57 | 50.36 |

Example 2

The meta-stable zone width was estimated by charging 800 grams of a solution containing 100 relative weight % cis-2,2,4,4-tetramethylcyclobutanediol and 69 relative weight % trans-2,2,4,4-tetramethylcyclobutanediol in isobutyl isobutyrate solvent to a 1.2 L jacketed glass vessel. The vessel was equipped with a 4-blade flat blade pitched impeller for solids suspension, and the jacket was used to control the temperature of the vessel contents. The vessel was equipped with charging and sampling ports on top and a valve at the base to drain the vessel. The vessel contents were heated to 90° C., at which temperature both isomers were completely in solution.

All measurements to estimate the meta-stable zone width were made using a Beckmann Instruments PC 800 Colorimeter device. The device operated by transmitting a white light source into the solution which was reflected from a mirror at a distance of several millimeters from the source back to a detector in the probe. When no particles were present in suspension, most of the light was reflected back to the detector. If the solution was relatively transparent, some of the light was adsorbed by the solution and some was diffracted, but the majority was reflected. If crystals were present, a substantial quantity of the white light was adsorbed by the crystal mass and diffracted and less of the light was reflected back to the detector. In order to calibrate the instrument, a reference intensity was measured when no crystals were in suspension, and this was referred to as the 100% transmittance level.

Figure 8:
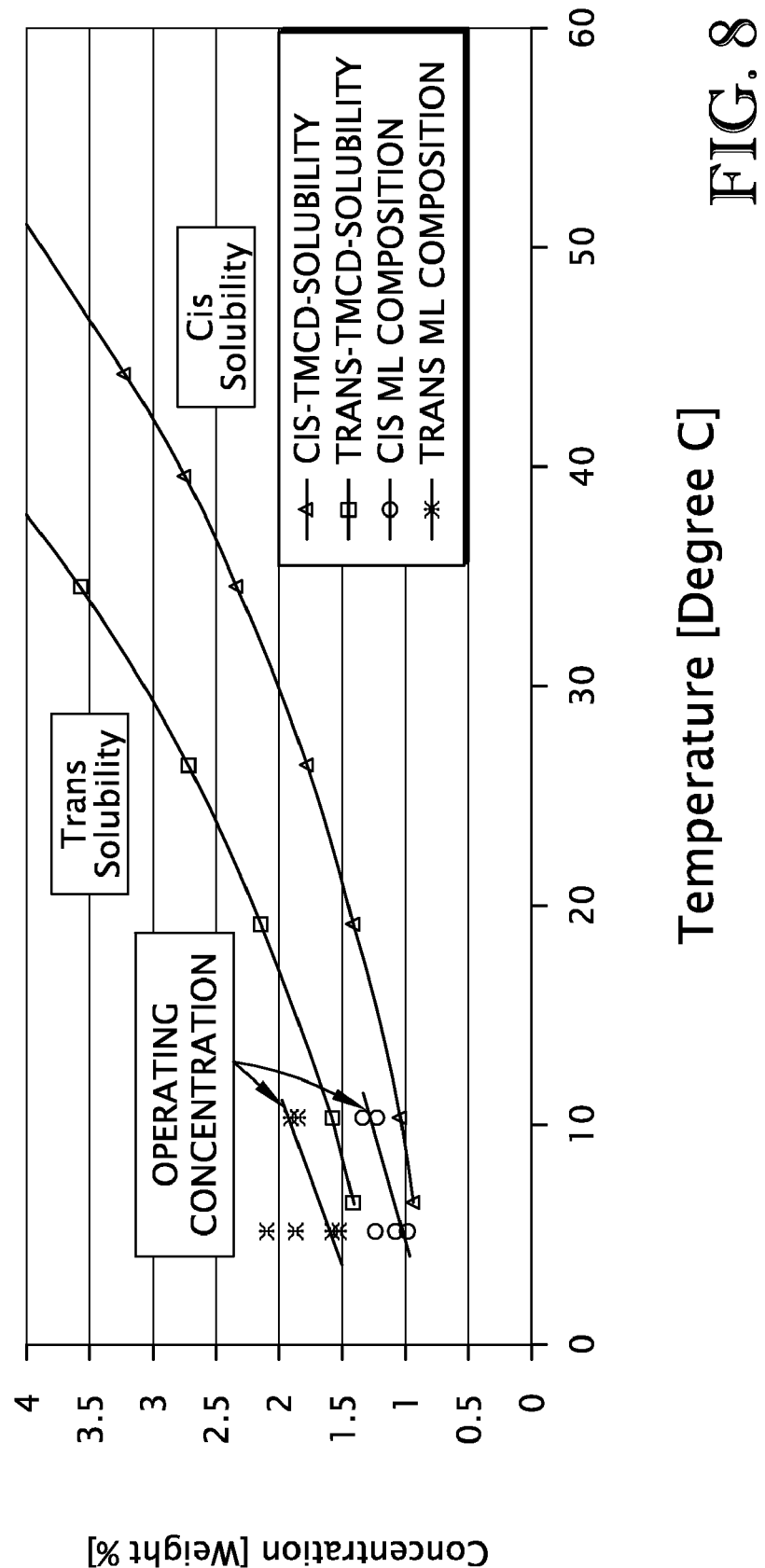
FIG. 8 is a graph showing the solubility of cis-and trans-2,2,4,4-tetramethylcyclobutanediol in isobutyl isobutyrate and operating points for continuous crystallization.

The colorimeter was placed in the vessel such that the probe tip was submerged in the solution. The crystal free solution was cooled from 90° C. to 10° C. at a pre-determined cooling rate indicated in Table 2 and the magnitude of the transmission signal of the white light source monitored. When crystals appeared in solution, the white light source was blocked and the transmission/reflection decreased rapidly. Two distinct step changes in the transmission signal were observed indicating the nucleation of cis- and trans-2,2,4,4-tetramethylcyclobutanediol in suspension. FIG. 8 is a graph showing the solubility of cis-and trans-2,2,4,4-tetramethyl-cyclobutanediol in isobutyl isobutyrate and operating points for continuous crystallization.

TABLE 2

Meta-stable zone width (MZW) of cis- and trans-2,2,4,4-tetramethylcyclobutanediol in isobutyl isobutyrate

| Experiment No. | Saturated Temperature Cis [° C.] | Saturated Temperature Trans [° C.] | Cooling Rate [° C./hr] | Cis Limit of MZW [° C.] | Trans Limit of MZW [° C.] | Cis MZW [° C.] | Trans MZW [° C.] |
|---|---|---|---|---|---|---|---|
| 1 | 68 | 57 | 15 | 50.94 | 48.67 | 17.06 | 8.33 |
| 2 | 68 | 57 | 10 | 51.77 | 49.29 | 16.23 | 7.71 |
| 3 | 68 | 57 | 5 | 60.38 | 50.34 | 7.62 | 6.66 |
| 4 | 68 | 57 | 5 | 58.24 | 50.36 | 9.76 | 6.64 |

By examining the results in Table 2, it can be seen that the width of the meta-stable region decreases as the cooling rate decreases. This was an expected result and is typical for systems of organic materials. The delay in the material crystallizing from solution is caused by an induction time delay caused by structural re-arrangement of the molecules comprising the substrate. This induction time is also a function of the micro properties of the solution such as turbulence fluctuations and the presence of impurities in solution. It is not unusual to see small differences in the onset of nucleation even when a solution is subjected to repeated cool-downs at the same cooling rate as shown by Experiments 3 and 4 in Table 2 where the onset of nucleation of the cis isomer differed by approximately 2° C. and the trans differed by 0.02° C.

Example 3

A number of semi-continuous experiments were conducted demonstrating the use of a continuous crystallization process to recover cis-2,2,4,4-tetramethylcyclobutanediol and trans-2,2,4,4-tetramethylcyclobutanediol from solution. The feed temperature was 70° C. All other operating conditions and composition of the feed material are shown in Tables 3 and 4 respectively. In table 4 (and table 7), the concentration of the cis and trans isomers are given in units of weight % relative to the solubility of each isomer at 62.6° C. The units of all other compounds are given in units of absolute weight %.

TABLE 3

Operating conditions for semi-continuous experiments

| Experiment Number | Number of Stages | Full Volume of each Vessel [L] | Active Volume in each Stage [L] | Feed Rate [mL/min] | Residence Time each Stage [Hours/Stage] | Transfer Rate [L/hr] | 1st Stage Temperature [° C.] | 2nd Stage Temp [° C.] |
|---|---|---|---|---|---|---|---|---|
| 1 | 2 | 4 | 1.0-2.0 | 34 | 1 | 0.9 | 45 | 5 |
| 2 | 2 | 4 | 1.0-2.0 | 34 | 1 | 0.9 | 45 | 5 |
| 3 | 1 | 4 | 1.0-2.0 | 25.5 | 0.75 | 0.68 | 10 | |

The crystallization was conducted on a laboratory scale using crystallizer active volumes of 2 liters. The feed composition given in Table 4 was pumped continuously to the first stage crystallizer and introduced into the crystallizer subsurface with respect to the active volume. The feed to the first stage crystallizer was a continuous feed stream. The product transfer between the first and second stage was intermittent (or "semi-continuous") and the product removal from the second stage was also intermittent.

The actual and active volumes of the laboratory scale crystallizers used during these experiments are described in Table 3. The term active volume refers to the actual volume of the equipment occupied by process fluid.

TABLE 4

Composition of the feed material

| Material | Composition Experiment Number 1 | Composition Experiment Number 2 | Composition Experiment Number 3 |
|---|---|---|---|
| | [Relative Wt %] | [Relative Wt %] | [Relative Wt %] |
| Cis-2,2,4,4-tetramethycyclobutanediol | 119% | 119% | 121% |
| Trans-2,2,4,4-tetramethycyclobutanediol | 82% | 86% | 86% |
| | [Abs Wt %] | [Abs Wt %] | [Abs Wt %] |
| Tetraethylene glycol dimethyl ether | 0.02 | 0.07 | 0.51 |
| Tetra methyl propane glycol | 0.29 | 0.31 | 0.29 |
| Triethylene glycol dimethyl ether | 0.04 | 0.08 | 0.00 |
| Cis-2,2,4,4-tetramethycyclo-butanediol-ester | 0.10 | 0.16 | 0.14 |
| Trans-2,2,4,4-tetramethycy-clobutanediol-ester | 0.04 | 0.01 | 0.00 |
| Isobutyl isobutyrate | 81.37 | 80.88 | 80.57 |
| Isobutryic acid | 0.08 | 0.12 | 0.12 |
| Di-isopropyl ketone | 0.07 | 0.08 | 0.07 |
| Methanol | 0.22 | 0.36 | 0.56 |

For cases where two stages of crystallization were used, transfers from the first stage to the second stage crystallizer were done in a semi-continuous fashion once every 30 minutes such that the average operating volume in each crystallizer did not change over a long period of time. Just before transfer of material from the first to the second stage crystallizer, an equal amount of material was removed from the second stage for filtration. The mass transferred between crystallizers and removed from the second stage crystallizer was approximately 900 grams each time. For experiments where only one stage was used, feed was pumped continuously and product removed in semi-continuous mode once every 22 minutes for filtration.

In the experiments where two stages were used, the crystallizers were each charged with material from a feed vessel and the contents in these vessels were cooled to the operating temperature of that stage of crystallization. Feed was then started to the first stage crystallizer, and then subsequently started to the second stage crystallizer. The system was allowed to operate in semi-continuous mode for a time period of at least 8 residence time equivalents. For example, in Experiment 1 from Table 3, in which the residence time of each stage was 1 hour, the crystallization time period was 8 hours. Allowing this amount of time during the start-up phase of crystallization is typical to achieve a steady-state situation. This was further demonstrated in Example 4.

The 900 grams of material from the second stage crystallizer were filtered on a vacuum filtration device having a coarse rated filtration element. Once the mother liquor had been filtered from the slurry, the remaining wet cake on filter was washed with an amount of cyclohexane approximately equivalent to the weight of material remaining on the filter. The cyclohexane had been chilled to 12° C. for this purpose. A large number of filtrations were conducted for each experiment. The average values for the typical filtration quantities are shown in Table 5.

(38.74 wt % for Experiment No. 3 versus 28.28 wt % for Experiment No. 1 and 22.99 wt % for Experiment No. 2). Higher moisture content results in higher drying energy requirements. The much higher moisture content is associated with the much greater void fraction in the cake as indicated by the difference in cake heights in Table 5. This difference in void fraction is typically caused by much smaller particle sizes in the original slurry.

The experiment with only one stage of crystallization was higher in trace compounds tetraethylene glycol dimethyl ether, methanol and isobutyl isobutyrate. Undesirable impurities may yield problems in downstream processes. While the higher quantity of tetraethylene glycol dimethyl ether in the product may be explained by the observed higher concentration in the feed material, this would not explain the presence of methanol and isobutyl isobutyrate.

Operating a process at lower final temperatures is beneficial from a yield point of view. The yield from the first two experiments that had a lower final temperature (5° C. versus 10° C.) resulted in a higher yield when compared with the final single-stage experiment. The mother liquor compositions for each experiment are shown in Table 7. Table 7 lists the mother liquor compositions (relative weight %) from experiments conducted at the operating points for continuous crystallization as shown in FIG. 8. FIG. 8 is a graph showing the relative solubility of cis- and trans-2,2,4,4-tetramethylcyclobutanediol in isobutyl isobutyrate and operating points for continuous crystallization. The operating points in FIG. 8 show the concentration of both cis- and trans-2,2,4,4-tetram-

TABLE 5

Average results from filtrations conducted for each set of experiments.

| Experiment No. | Slurry Charged to Filter [gr] | Mother liquor Recovered [gr] | Cake Height [mm] | Wash Material Temperature [° C.] | Wash Quantity [gr] | Wash Collected [gr] | Wet Solids Recovered [gr] |
|---|---|---|---|---|---|---|---|
| 1 | 859 | 711 | 52 | 13 | 173 | 179 | 128 |
| 2 | 918 | 745 | 55 | 18 | 192 | 211 | 133 |
| 3 | 1024 | 797 | 95 | 18 | 238 | 252 | 188 |

At this point, samples of the washed wet cake were removed from the filter and analyzed for composition. The average results are shown in Table 6. From these results, the yield of product could also be calculated, also shown in Table 6.

ethylcyclobutanediol in mother liquor samples, i.e., the mother liquor that was separated from the solids during the slurry filtration process. The concentration of both cis and trans-2,2,4,4-tetramethylcyclobutanediol was relatively constant for each Experiment (Nos. 1, 2 or 3) and the concentra-

TABLE 6

Average composition of wet solids from filtration experiments

| Experiment Number | Cis-2,2,4,4-tetramethyl-cyclobutanediol [wt %] | Trans-2,2,4,4-tetramethyl-cyclobutanediol [wt %] | Tetraethylene glycol dimethyl ether [ppm] | Isobutyl isobutyrate [ppm] | Methanol [wt %] | Moisture [wt %] | Cis Yield [wt %] | Trans Yield [wt %] |
|---|---|---|---|---|---|---|---|---|
| 1 | 51.75 | 48.03 | 0.00 | 2152.74 | 1.06 | 28.28% | 81.67% | 79.22% |
| 2 | 55.37 | 44.40 | 0.00 | 2312.78 | 0.66 | 22.99% | 83.78% | 85.96% |
| 3 | 50.16 | 48.88 | 5675.00 | 2453.99 | 1.47 | 38.74% | 77.73% | 75.68% |

As shown in Table 6, the moisture content for the process with only one stage resulted in a higher moisture content tion of isomer being a reflection of the constant operating temperature of the final stage of crystallization. In Experiment No. 3, in which the operating temperature of the single stage crystallization process was 10° C., the overall concentrations were higher.

TABLE 7

Mother liquor compositions from experiments

| | Experiment | | | | | | | | | | | |
|---|---|---|---|---|---|---|---|---|---|---|---|---|
| | 1 | 1 | 1 | 1 | 1 | 1 | 1 | 1 | 1 | 1 | 1 | 1 |
| Temperature [° C.] | 5 | 5 | 5 | 5 | 5 | 5 | 5 | 5 | 5 | 5 | 5 | 5 |
| Cis-Composition [Relative wt %] | 5.7 8 | 5.7 8 | 5.7 8 | 5.7 8 | 5.7 8 | 5.7 8 | 5.7 8 | 5.7 8 | 5.7 8 | 5.7 8 | 5.7 8 | 5.7 8 |
| Trans Composition [Relative wt %] | 6.5 5 | 6.5 5 | 6.5 5 | 6.5 5 | 6.5 5 | 6.5 5 | 6.5 5 | 6.5 5 | 6.5 5 | 6.5 5 | 6.5 5 | 6.5 5 |

| | Experiment | | | | | | | | | | | |
|---|---|---|---|---|---|---|---|---|---|---|---|---|
| | 1 | 2 | 2 | 2 | 2 | 2 | 2 | 3 | 3 | 3 | 3 | 3 |
| Temperature [° C.] | 5 | 5 | 5 | 5 | 5 | 5 | 5 | 5 | 5 | 5 | 5 | 5 |
| Cis-Composition [Relative wt %] | 1.1 2 | 1.1 2 | 1.1 2 | 1.1 2 | 1.1 2 | 1.1 2 | 1.1 2 | 1.1 2 | 1.1 2 | 1.1 2 | 1.1 2 | 1.1 2 |
| Trans Composition [Relative wt %] | 1.0 8 | 1.0 8 | 1.0 8 | 1.0 8 | 1.0 8 | 1.0 8 | 1.0 8 | 1.0 8 | 1.0 8 | 1.0 8 | 1.0 8 | 1.0 8 |

Example 4

Another set of semi-continuous experiments were conducted demonstrating the use of a continuous crystallization process to recover cis-2,2,4,4-tetramethylcyclobutanediol and trans-2,2,4,4-tetramethylcyclobutanediol from solution. The temperature of the feed was 70° C. All other operating conditions and composition of the feed material are shown in Tables 8 and 9 respectively. In table 9 (and table 10), the concentration of the cis and trans isomers are given in units of weight % relative to the solubility of each isomer at 62.6° C. The units of all other compounds are given in units of absolute weight %.

TABLE 8

Operating conditions for semi-continuous experiments

| Experiment Number | Number of Stages [##] | Full Volume of each Vessel [L] | Active Volume in each Stage [L] | Feed Rate [mL/min] | Residence Time each Stage [Hours/Stage] | Transfer Rate [L/hr] | 1st Stage Temperature [° C.] | 2nd Stage Temperature [° C.] |
|---|---|---|---|---|---|---|---|---|
| 1 | 2 | 4 | 1.5-2.5 | 17 | 2 | 0 | 55 | 5 |
| 2 | 2 | 4 | 1.5-2.5 | 34 | 1 | 2 | 55 | 5 |
| 3 | 1 | 4 | 2.5-3.5 | 25 | 2 | 1.33 | 1 | 11 |

TABLE 9

Composition of the feed material

| | Material | | |
|---|---|---|---|
| | Composition [Relative wt %] | Composition [Relative wt %] | Composition [Relative wt %] |
| Experiment Number | 1 | 2 | 3 |
| Cis-2,2,4,4-tetramethylcyclobutanediol | 170 | 184 | 224 |
| Trans-2,2,4,4-tetramethylcyclobutanediol | 170 | 121 | 135 |

These experiments were conducted to demonstrate the effect of residence time and the number of stages on the properties of the resulting filter cake. Only 2.5 residence time equivalents were employed in each experiment before slurry was removed from the final stage of operation for filtration. A number of filtrations were conducted for each experiment. The average results of the filtrations carried out are listed in Tables 10 and 11, showing the mother liquor and solids composition respectively.

TABLE 10

Compositions of mother liquor streams from the filtrations

| Experiment Number | Type | Cis-2,2,4,4-tetramethyl-cyclobutanediol [Relative wt %] | Trans-2,2,4,4-tetramethyl-cyclobutanediol [Relative wt %] |
|---|---|---|---|
| 1 | Mother Liquor | 3.87 | 4.51 |
| 2 | Mother Liquor | 3.51 | 4.14 |
| 3 | Mother Liquor | 3.51 | 4.14 |

TABLE 11

Compositions of filtered, washed and dried solids from the filtrations

| Experiment Number | Type | Cis-2,2,4,4-tetramethylcyclobutanediol [Absolute wt %] | Trans-2,2,4,4-tetramethylcyclobutanediol [Absolute wt %] | Isobutyl isobutyrate [Absolute wt %] | Heptane [Absolute wt %] |
|---|---|---|---|---|---|
| 1 | Dried Solids | 54.39 | 45.32 | 0.07 | 0.03 |
| 2 | Dried Solids | 56.23 | 43.53 | 0.05 | 0.04 |
| 3 | Dried Solids | 56.96 | 42.75 | 0.08 | 0.01 |

In addition, Table 12 shows several filtration parameters representative of the filtration properties of the cake. These are the specific cake resistance and the cake resistance. Cake resistance (r, m$^{-2}$), which is a volumetric measure of cake resistance, is defined as the inverse of the cake permeability (B, m$^2$). The cake permeability is defined as:

$$r = \frac{1}{B} = \frac{P}{u\mu L}$$

where,

L=cake thickness, m u=superficial velocity of fluid through cake, m/s

P=the pressuredrop across the cake, Pa

µ=dynamic viscosity of the mother liquor, Pa·s

The specific cake resistance (R, m/kg) is a mass based measure of cake resistance and is given by the formula:

$$R = \frac{1}{B\rho_s(1-e)} = \frac{P}{u\mu L\rho_s(1-e)}$$

where, $\rho_s$=density of the solids, kg/m$^3$ e=cake porosity, (volume of voids in cake/volume of cake).

These definitions are well known in the literature and can be reviewed in a standard chemical engineering textbook, such as in Perry's Chemical Engineers Handbook, 7$^{th}$ edition, editors Robert H. Perry, Don W. Green, McGraw-Hill, 1997, "Filtration," p. 18-74, whose disclosure regarding the definitions of cake resistance and specific cake resistance is incorporated herein by reference.

A low value of cake resistance or specific cake resistance means that the filter cake will filter more rapidly. Cake resistance or specific cake resistance can be readily calculated using standard measures of cake filtration performance, such as the weights and volumes of all feed and product streams to and from the filter, the densities of all feed and product streams to and from the filter, the volumetric rate at which mother liquor drains from the cake under a given vacuum or pressure, the height of the filter cake on the filter, and the dimensions of the filtration device. In this Example, the 2.5 residence time equivalents were not sufficient to allow the experiments to reach a steady-state. Instead, as shown in Table 12, the cake resistance decreased from one experiment to the next indicating that the process was still in a dynamic phase of operation.

TABLE 12

Filtration cake properties

| Experiment Number | Specific Cake Resistance (R) [m/kg] | Cake Resistance (r) [m$^{-2}$] |
|---|---|---|
| 1 | 2.07E+08 | 1.17E+11 |
| 2 | 1.48E+08 | 6.96E+10 |
| 3 | 1.10E+08 | 4.45E+10 |

The invention has been described in detail with reference to the embodiments disclosed herein, but it will be understood that variations and modifications can be effected within the spirit and scope of the invention.

I claim:

1. A process for the continuous crystallization of a mixture comprising cis-2,2,4,4-tetramethylcyclobutanediol and trans-2,2,4,4-tetramethylcyclobutanediol dissolved in a solvent, the process comprising:
   (a) crystallizing cis-2,2,4,4-tetramethylcyclobutanediol in a first crystallization stage operated at a temperature such that the concentration of trans-2,2,4,4-tetramethylcyclobutanediol in solution is below the saturated concentration of trans-2,2,4,4-tetramethylcyclobutanediol at the operating temperature of the first stage;
   (b) transferring a slurry of crystallized cis-2,2,4,4-tetramethylcyclobutanediol and the corresponding mother liquor from the first crystallization stage to a second crystallization stage;
   (c) crystallizing both cis-2,2,4,4-tetramethylcyclobutanediol and trans-2,2,4,4-tetramethylcyclobutanediol in the second crystallization stage; and
   (d) separating the crystals of cis-2,2,4,4-tetramethylcyclobutanediol and trans-2,2,4,4-tetramethylcyclobutanediol from the mother liquor present in the second crystallization stage to yield a mixture of crystallized cis-2,2,4,4-tetramethylcyclobutanediol and crystallized trans-2,2,4,4-tetramethylcyclobutanediol, wherein the solvent is isobutyl isobutyrate.

2. The process according to claim 1, wherein the mixture comprising cis-2,2,4,4-tetramethylcyclobutanediol and trans-2,2,4,4-tetramethylcyclobutanediol dissolved in the solvent is the result of the hydrogenation of 2,2,4,4-tetramethylcyclobutanedione.

3. The process according to claim 1, wherein the concentration of cis-2,2,4,4-tetramethylcyclobutanediol in the mixture ranges from 5 to 25 wt % with respect to the total weight of the mixture and the concentration of trans-2,2,4,4-tetramethylcyclobutanediol in the mixture ranges from 5 to 25 wt % with respect to the total weight of the mixture.

4. The process according to claim 1, wherein the residence time in each crystallization stage is independently at least 0.5 hours.

5. The process according to claim 4, wherein the residence time in each crystallization stage is independently from 0.5 to four hours.

6. The process according to claim 5, wherein the residence time in each crystallization stage is independently from one to three hours.

7. The process according to claim 1, wherein the combined purity of the mixture of isolated, dried crystallized cis- and trans-2,2,4,4-tetramethylcyclobutanediol is at least 99.8%.

8. The process according to claim 1, further comprising transferring the slurry of crystallized 2,2,4,4-tetramethylcyclobutanediol from the first crystallization stage to the second crystallization stage independently from the transfer of the mother liquor from the first crystallization stage to the second crystallization stage.

9. The process according to claim 8, wherein the mixture comprising cis-2,2,4,4-tetramethylcyclobutanediol and trans-2,2,4,4-tetramethylcyclobutanediol dissolved in the solvent is the result of the hydrogenation of 2,2,4,4-tetramethylcyclobutanedione.

10. The process according to claim 8, wherein the concentration of cis-2,2,4,4-tetramethylcyclobutanediol in the mixture ranges from 5 to 25 wt % with respect to the total weight of the mixture and the concentration of trans-2,2,4,4-tetramethylcyclobutanediol in the mixture ranges from 5 to 25 wt % with respect to the total weight of the mixture.

11. The process according to claim 8, wherein the residence time in each crystallization stage is independently from 0.5 to four hours.

12. The process according to claim 11, wherein the residence time in each crystallization stage is independently from one to three hours.

13. The process according to claim 8, further comprising removing crystallized cis-2,2,4,4-tetramethylcyclobutanediol from the first crystallization stage to yield solid cis-2,2,4,4-tetramethylcyclobutanediol.

14. The process according to claim 8, wherein the rate of transfer of the slurry of crystallized 2,2,4,4-tetramethylcyclobutanediol from the first crystallization stage to the second crystallization stage is slower than the rate of the transfer of the mother liquor from the first crystallization stage to the second crystallization stage.

15. The process according to claim 8, wherein the combined purity of the mixture of isolated, dried crystallized cis- and trans-2,2,4,4- tetramethylcyclobutanediol is at least 99.8%.

16. The process according to claim 1, further comprising:
  (a) recycling a fraction of the mixture of crystallized cis and trans 2,2,4,4-tetramethylcyclobutanediol from the second crystallization stage to the first crystallization stage; and
  (b) growing crystals of cis-2,2,4,4-tetramethylcyclobutanediol in the first crystallization stage.

17. The process according to claim 16, wherein the mixture comprising cis-2,2,4,4-tetramethylcyclobutanediol and trans-2,2,4,4-tetramethylcyclobutanediol dissolved in the solvent is the result of the hydrogenation of 2,2,4,4-tetramethylcyclobutanedione.

18. The process according to claim 16, wherein the concentration of cis-2,2,4,4-tetramethylcyclobutanediol in the mixture ranges from 5 to 25 wt % with respect to the total weight of the mixture and the concentration of trans-2,2,4,4-tetramethylcyclobutanediol in the mixture ranges from 5 to 25 wt % with respect to the total weight of the mixture.

19. The process according to claim 16, wherein the residence time in each crystallization stage is independently at least 0.5 hours.

20. The process according to claim 19, wherein the residence time in each crystallization stage is independently from 0.5 to four hours.

21. The process according to claim 20, wherein the residence time in each crystallization stage is independently from one to three hours.

22. A process for the continuous crystallization of a mixture comprising cis-2,2,4,4-tetramethylcyclobutanediol and trans-2,2,4,4-tetramethylcyclobutanediol dissolved in a solvent, the process comprising:
  (a) crystallizing cis-2,2,4,4-tetramethylcyclobutanediol in a first crystallization stage operated at a temperature such that the concentration of trans-2,2,4,4-tetramethylcyclobutanediol in solution is below the saturated concentration of trans-2,2,4,4-tetramethylcyclobutanediol;
  (b) separating the crystals of the cis-2,2,4,4-tetramethylcyclobutanediol from the mother liquor present in the first crystallization stage;
  (c) removing the crystallized the cis-2,2,4,4-tetramethylcyclobutanediol to yield solid 2,2,4,4-tetramethylcyclobutanediol;
  (d) transferring mother liquor obtained from the separation of crystals to a second crystallization stage;
  (e) crystallizing both cis-2,2,4,4-tetramethylcyclobutanediol and trans-2,2,4,4-tetramethylcyclobutanediol in the second crystallization stage; and
  (f) separating the crystals from the mother liquor present in the second crystallization stage to yield a mixture of solid cis-2,2,4,4-tetramethylcyclobutanediol and solid trans-2,2,4,4-tetramethylcyclobutanediol, wherein the solvent is isobutyl isobutyrate.

23. The process according to claim 22, wherein the mixture comprising cis-2,2,4,4-tetramethylcyclobutanediol and trans-2,2,4,4-tetramethylcyclobutanediol dissolved in the solvent is the result of the hydrogenation of 2,2,4,4-tetramethylcyclobutanedione.

24. The process according to claim 22, wherein the concentration of cis-2,2,4,4-tetramethylcyclobutanediol in the mixture to be subjected to crystallization is from 5 to 25 wt % with respect to the total weight of the mixture and the concentration of trans-2,2,4,4-tetramethylcyclobutanediol in the mixture to be subjected to crystallization is from 5 to 25 wt % with respect to the total weight of the mixture.

25. The process according to claim 22, wherein the residence time in each crystallization stage is independently at least 0.5 hours.

26. The process according to claim 25, wherein the residence time in each crystallization stage is independently from 0.5 to four hours.

27. The process according to claim 26, wherein the residence time in each crystallization stage is independently from one to three hours.

28. The process according to claim 22, wherein the combined purity of the mixture of isolated, dried crystallized cis- and trans-2,2,4,4-tetramethylcyclobutanediol is at least 99.8%.

29. The process according to claim 22, further comprising:
  (a) recycling a fraction of the mixture of crystallized cis and trans 2,2,4,4-tetramethylcyclobutanediol from the second crystallization stage to the first crystallization stage; and
  (b) growing crystals of cis-2,2,4,4-tetramethylcyclobutanediol in the first crystallization stage.

30. The process according to claim 29, wherein the mixture comprising cis-2,2,4,4-tetramethylcyclobutanediol and trans-2,2,4,4-tetramethylcyclobutanediol dissolved in the solvent is the result of the hydrogenation of 2,2,4,4-tetramethylcyclobutanedione.

31. The process according to claim 29, wherein the concentration of cis-2,2,4,4-tetramethylcyclobutanediol in the mixture to be subjected to crystallization is from 5 to 25 wt % with respect to the total weight of the mixture and the concentration of trans-2,2,4,4-tetramethylcyclobutanediol in the mixture to be subjected to crystallization is from 5 to 25 wt % with respect to the total weight of the mixture.

32. The process according to claim 29, wherein the residence time in each crystallization stage is independently from 0.5 to four hours.

33. The process according to claim 32, wherein the residence time in each crystallization stage is independently from one to three hours.

34. The process according to claim 29, wherein the combined purity of the mixture of isolated, dried crystallized cis- and trans-2,2,4,4-tetramethylcyclobutanediol is at least 99.8%.

35. The process according to claim 29, wherein the crystallized 2,2,4,4-tetramethylcyclobutanediol from the second crystallization stage is completely recycled to the first crystallization stage.

36. The process according to claim 35, wherein the mixture comprising cis-2,2,4,4-tetramethylcyclobutanediol and trans-2,2,4,4-tetramethylcyclobutanediol dissolved in the solvent is the result of the hydrogenation of 2,2,4,4-tetramethylcyclobutanedione.

37. The process according to claim 35, wherein the concentration of cis-2,2,4,4-tetramethylcyclobutanediol in the mixture ranges from 5 to 25 wt % with respect to the total weight of the mixture and the concentration of trans-2,2,4,4-tetramethylcyclobutanediol in the mixture ranges from 5 to 25 wt % with respect to the total weight of the mixture.

38. The process according to claim 35, wherein the residence time in each crystallization stage is independently at least 0.5 hours.

39. The process according to claim 38, wherein the residence time in each crystallization stage is independently from 0.5 to four hours.

40. The process according to claim 39, wherein the residence time in each crystallization stage is independently from one to three hours.

41. The process according to claim 35, wherein the combined purity of the mixture of isolated, dried crystallized cis- and trans-2,2,4,4-tetramethylcyclobutanediol is at least 99.8%.

* * * * *